United States Patent [19]

Kraatz et al.

[11] 4,330,547
[45] May 18, 1982

[54] COMBATTING FUNGI WITH TRIAZOLYLPHENACYL PYRIDYL ETHER DERIVATIVES

[75] Inventors: Udo Kraatz, Leverkusen; Karl H. Büchel, Burscheid; Jörg Stetter, Wuppertal; Paul-Ernst Frohberger, Leverkusen; Wilhelm Brandes, Leichlingen, all of Fed. Rep. of Germany

[73] Assignee: Bayer Aktiengesellschaft, Leverkusen, Fed. Rep. of Germany

[21] Appl. No.: 217,948

[22] Filed: Dec. 18, 1980

[30] Foreign Application Priority Data

Jan. 5, 1980 [DE] Fed. Rep. of Germany ....... 3000244

[51] Int. Cl.³ .................... C07D 401/12; A01N 43/40
[52] U.S. Cl. ..................................... 424/263; 546/276
[58] Field of Search ......................... 546/276; 424/263

[56] References Cited

U.S. PATENT DOCUMENTS 4,166,854  9/1979  Carson et al. ....................... 546/276

Primary Examiner—John M. Ford
Attorney, Agent, or Firm—Sprung, Horn, Kramer & Woods

[57] ABSTRACT

Triazolylphenacyl pyridyl ether derivatives of the formula

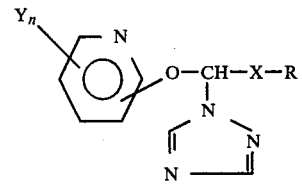

in which
R is optionally substituted phenyl,
X is —CO— or CH(OH)—,
Y each independently is halogen, alkyl, alkoxy or cyano, and
n is 0, 1, 2, 3 or 4, or a physiologically acceptable addition product thereof with an acid or metal salt which exhibit fungicidal activity.

10 Claims, No Drawings

COMBATTING FUNGI WITH TRIAZOLYLPHENACYL PYRIDYL ETHER DERIVATIVES

The present invention relates to certain new triazolylphenacyl pyridyl ether derivatives, to a process for their preparation and to their use as fungicides.

It has already been disclosed that such azolylalkyl pyridyl ether derivatives as, for example, substituted 1-pyridyloxy-3,3-dimethyl-1-triazolyl- or -imidazolyl-butan-2-ones or -ols, have a good fungicidal activity (see U.S. patent application Ser. No. 964,768, filed Nov. 29, 1978, now pending). However, their action is not always completely satisfactory, especially when small amounts and low concentrations are applied.

The present invention now provides, as new compounds, the triazolylphenacyl pyridyl ether derivatives of the general formula

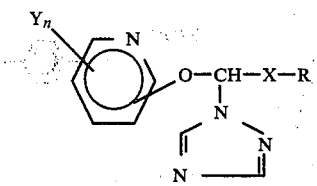

(I)

in which
R represents optionally substituted phenyl,
X represents the keto group or a CH(OH)— grouping,
Y represents halogen, alkyl, alkoxy or cyano and
n represents 0, 1, 2, 3 or 4,
and physiologically acceptable acid addition salts and metal salt complexes thereof.

Those compounds of the formula (I) in which X represents the CH(OH)— group have two asymmetric carbon atoms; they can therefore exist in the form of the two geometric isomers (erythro-form and threo-form), which can be obtained in different proportions. In both cases, they are in the form of optical isomers. Formula (I) encompasses all of the possible isomers.

The invention also provides a process for the preparation of a triazolylphenacyl pyridyl ether derivative of the formula (I) in which (a) a triazolylhalogeno-ketone of the general formula

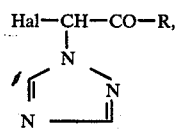

(II)

in which
R has the meaning indicated above and
Hal represents chlorine or bromine,
is reacted with a pyridinol of the general formula

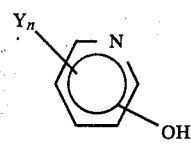

(III)

in which

Y and n have the meanings indicated above,
in the presence of an acid-binding agent and in the presence of a diluent, or (b) a halogenoether-ketone of the general formula

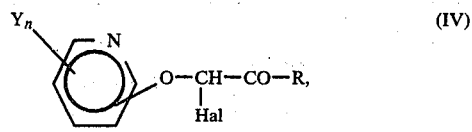

(IV)

in which
Hal, R, Y and n have the meanings indicated above, is reacted with 1,2,4-triazole in the presence of an acid-binding agent and if appropriate in the presence of a diluent, or (c), if required, the ketone derivative obtainable according to process variant (a) or (b), of the general formula

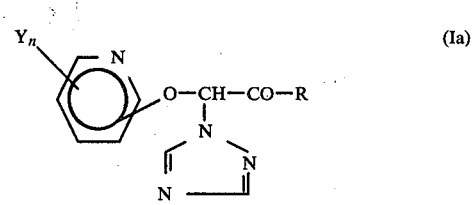

(Ia)

in which
R, Y and n have the meaning indicated above,
is reduced by known methods in the customary manner.

An acid or a metal salt can then optionally be added onto the compound of the formula (I) obtained in process variant (a), (b) or (c).

The triazolylphenacyl pyridyl ether derivatives of the formula (I) have powerful fungicidal properties. Surprisingly, the compounds according to the invention exhibit a better fungicidal activity than the substituted 1-pyridyloxy-3,3-dimethyl-1-triazolyl- or -imidazolyl-butan-2-ones or -ols which are known from the state of the art and are closely related compounds chemically and from the point of view of their action. The substances according to the invention thus represent an enrichment of the art.

The formula (I) provides a general definition of the triazolylphenacyl pyridyl ether derivatives according to the invention. Preferably, in this formula, R represents phenyl which optionally carries one or more substituents selected independently from halogen, straight-chain or branched alkyl and alkoxy with in either case 1 to 4 carbon atoms and phenyl and phenoxy, in either case optionally substituted by halogen, and Y represents halogen, straight-chain or branched alkyl or alkoxy with in either case 1 to 4 carbon atoms or cyano. X and the index n preferably have the meanings given in the definition of the invention.

Very particularly preferred compounds of the formula (I) are those in which R represents phenyl which is optionally monosubstituted or disubstituted by identical or different substituents selected from fluorine, chlorine, bromine, methyl, methoxy, phenyl, phenoxy, chlorophenyl and chlorophenoxy; Y represents fluorine, chlorine, bromine, iodine, methyl, methoxy or cyano; and X and the index n have the meanings given in the definition of the invention.

The following compounds of the general formula (I) may be mentioned specifically, in addition to the compounds mentioned later in the preparative examples:
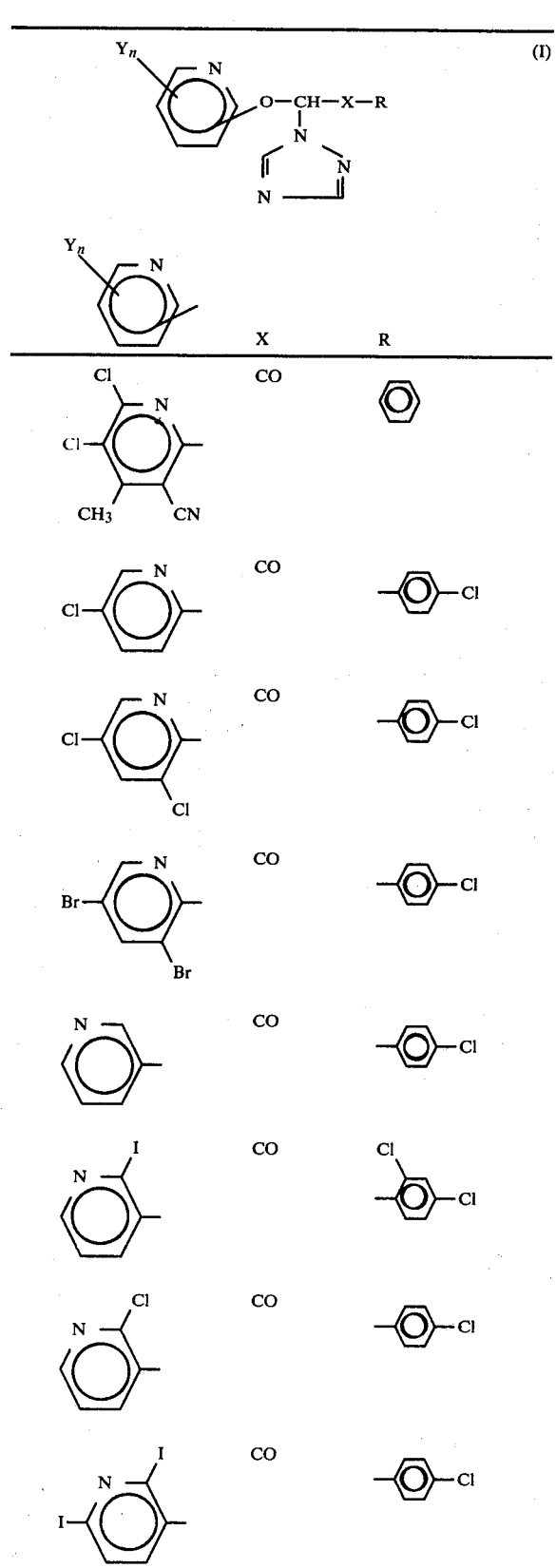
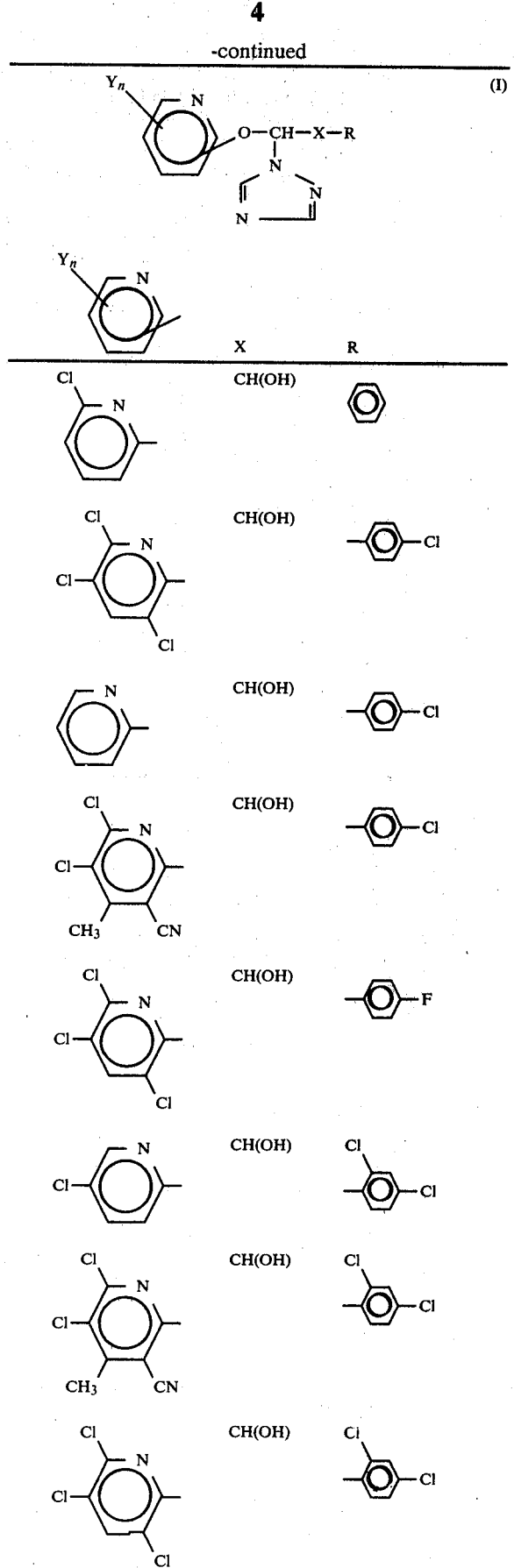

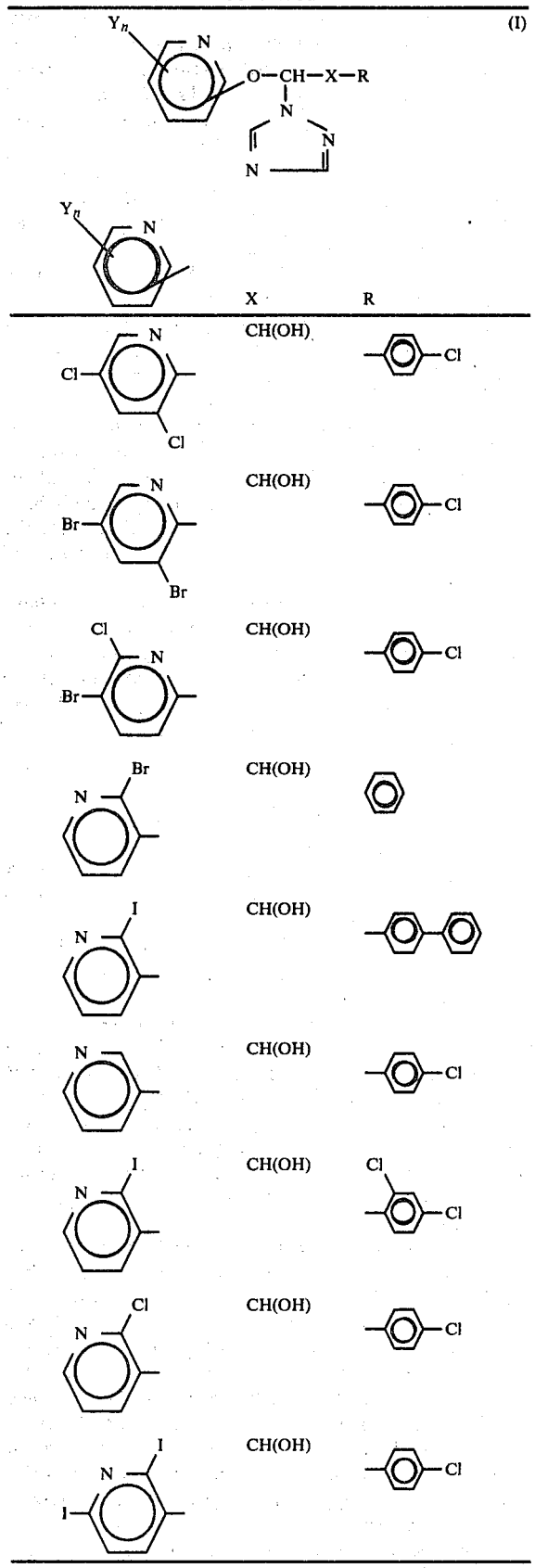
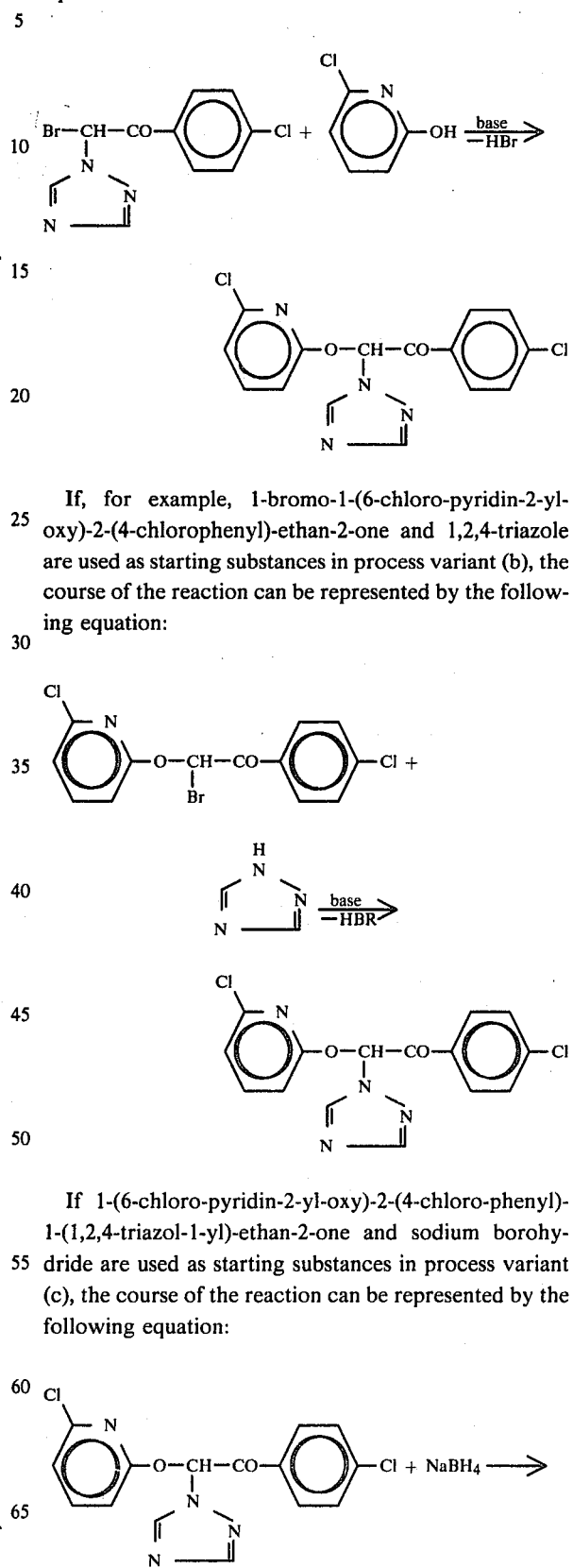

If, for example, ω-bromo-ω-(1,2,4-triazol-1-yl)-4-chloroacetophenone and 6-chloro-pyridin-2-ol are used as starting substances in process variant (a), the course of the reaction can be represented by the following equation:

If, for example, 1-bromo-1-(6-chloro-pyridin-2-yl-oxy)-2-(4-chlorophenyl)-ethan-2-one and 1,2,4-triazole are used as starting substances in process variant (b), the course of the reaction can be represented by the following equation:

If 1-(6-chloro-pyridin-2-yl-oxy)-2-(4-chloro-phenyl)-1-(1,2,4-triazol-1-yl)-ethan-2-one and sodium borohydride are used as starting substances in process variant (c), the course of the reaction can be represented by the following equation:

-continued

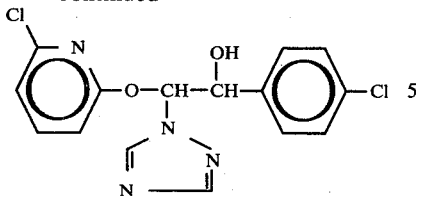

The formula (II) provides a general definition of the triazolylhalogeno-ketones to be used as starting substances for process variant (a). In this formula, R preferably represents those radicals which have already been mentioned as preferred therefor in connection with the description of the substances of the formula (I).

The triazolylhalogeno-ketones of the formula (II) are the subject of application Ser. No. 182,357, filed Aug. 29, 1980, now pending. They are obtained by a process in which known triazolyl ketones (see application Ser. No. 586,121, filed June 11, 1975, now abandoned) of the general formula

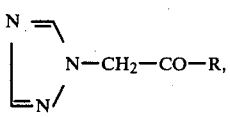  (V)

in which

R has the meaning indicated above,
are reacted with bromine or chlorine in the presence of an acid solvent, such as, in particular, glacial acetic acid, and in the presence of a hydrogen halide acceptor, for example sodium hydroxide or acetate, at temperatures between 20° and 100° C. The triazolylhalogeno-ketones of the formula (II) so formed can be further reacted directly.

Examples of starting substances of the formula (II) which may be mentioned are: ω-bromo(chloro)-ω-(1,2,4-triazol-1-yl)-acetophenone, ω-bromo(chloro)-ω-(1,2,4-triazol-1-yl)-4-chloroacetophenone, ω-bromo(chloro)-ω-(1,2,4-triazol-1-yl)-4-fluoroacetophenone, ω-bromo(chloro)-ω-(1,2,4-triazol-1-yl)-2-chloroacetophenone, ω-bromo(chloro)-ω-(1,2,4-triazol-1-yl)-2-methylacetophenone, ω-bromo(chloro)-ω-(1,2,4-triazol-1-yl)-2,4-dichloroacetophenone, ω-bromo(chloro)-ω-(1,2,4-triazol-1-yl)-4-phenylacetophenone, ω-bromo(chloro)-ω-(1,2,4-triazol-1-yl)-4-(4'-chlorophenylacetophenone) and ω-bromo(chloro)-ω-(1,2,4-triazol-1-yl)-4-phenoxyacetophenone.

The formula (III) provides a general definition of the pyridinols also to be used as starting substances for process variant (a). In this formula, Y and the index n preferably have those meanings which have already been mentioned as preferred therefor in connection with the description of the substances of the formula (I). If appropriate, the pyridinols of the formula (III) are also employed in the form of their silver salts.

The pyridinols of the formula (III) are generally known compounds of organic chemistry. Examples which may be mentioned are: 2-hydroxy-pyridine, 3-hydroxypyridine, 4-hydroxy-pyridine, 2-hydroxy-6-chloro-pyridine, 3-hydroxy-5-chloro-pyridine, 2-hydroxy-4-chloro-pyridine, 2-hydroxy-3-chloro-pyridine, 2-hydroxy-6-bromo-pyridine, 2-hydroxy-5-bromo-pyridine, 2-hydroxy-4-bromo-pyridine, 2-hydroxy-3-bromo-pyridine, 2-hydroxy-6-methyl-pyridine, 2-hydroxy-5-methyl-pyridine, 2-hydroxy-4-methylpyridine, 2-hydroxy-3-methyl-pyridine, 2-hydroxy-6-fluoro-pyridine, 2-hydroxy-5-fluoro-pyridine, 2-hydroxy-4-fluoro-pyridine, 2-hydroxy-3-fluoro-pyridine, 3-hydroxy-2-chloro-pyridine, 3-hydroxy-2-bromo-pyridine, 3-hydroxy-2-fluoro-pyridine, 3-hydroxy-2-iodo-pyridine, 3-hydroxy-2-methoxy-pyridine, 3-hydroxy-6-chloro-pyridine, 3-hydroxy-5-chloro-pyridine, 4-hydroxy-2-chloro-pyridine, 4-hydroxy-pyridine, 4-hydroxy-3-chloro-pyridine, 2-hydroxy-3,5,6-trichloropyridine, 2-hydroxy-3-cyano-5,6-dichloro-4-methyl-pyridine, 2-hydroxy-5-bromo-6-chloro-pyridine, 2-hydroxy-5-chloro-4,6-dimethyl-3-cyano-pyridine, 2-hydroxy-3,5-dichloropyridine, 2-hydroxy-5-bromo-4,6-dimethyl-3-cyano-pyridine, 3-hydroxy-2,6-diiodo-pyridine, 2-hydroxy-3,5-dibromo-6-chloropyridine and 2-hydroxy-5-bromo-6-chloro-3-cyano-4-methylpyridine.

The formula (IV) provides a general definition of the halogenoether-ketones to be used as starting substances for process variant (b). In this formula, R, Y and the index n preferably have those meanings which have already been mentioned as preferred for these variables in connection with the description of the substances of the formula (I).

The halogenoether-ketones of the formula (IV) have not hitherto been disclosed in the literature, but they can be prepared by known processes, by a procedure in which pyridinols of the (III) are reacted with known halogeno-ketones (see application Ser. No. 586,121 supra) of the general formula $$Hal-CH_2-CO-R \qquad (VI),$$

in which

Hal and R have the meanings indicated above,
in the presence of an acid-binding agent, for example potassium carbonate, and in the presence of an inert organic solvent, for example acetone, at temperatures between 60° and 120° C. One of the two active hydrogen atoms is then replaced by chlorine or bromine in the customary manner.

Possible diluents for the reactions in process variants (a) and (b) are inert organic solvents. These include, as preferences, ketones, such as diethyl ketone, and in particular acetone and methyl ethyl ketone; nitriles, such as propionitrile, and in particular acetonitrile; alcohols, such as ethanol or isopropanol; ethers, such as tetrahydrofuran or dioxane; benzene; formamides, such as, in particular, dimethylformamide; and halogenated hydrocarbons.

The reactions in process variants (a) and (b) are carried out in the presence of an acid-binding agent. It is possible to add any of the inorganic or organic acid-binding agents which can customarily be used, such as alkali metal carbonates, for example sodium carbonate, potassium carbonate and sodium bicarbonate, or such as silver carbonate, or such as lower tertiary alkylamines, cycloalkylamines or aralkylamines, for example triethylamine or dimethylbenzylamine; or such as pyridine and diazabicyclooctane. In process variant (b), it is also possible to use an appropriate excess of the azole used as a starting material.

The reaction temperatures can be varied within a substantial range in process variants (a) and (b). In general, the reaction is carried out between about 20° and about 150° C., preferably at 60° to 120° C. If a solvent is present, the reaction is appropriately carried out at the boiling point of the particular solvent.

In carrying out process variant (a) or (b), 1 to 2 mols of pyridinol of the formula (III) or 1 to 2 mols of 1,2,4-triazole and in each case 1 to 2 mols of acid-binding agent are preferably employed per mol of the compound of the formula (II) or (IV). To isolate the compound of the formula (I), the solvent is distilled off, and either water is added to the residue and the mixture is stirred vigorously, whereupon the reaction product crystallizes completely, or the residue is taken up in a mixture of an organic solvent and water and the organic phase is separated off, washed with water, dried over sodium sulphate and freed from solvent in vacuo. If appropriate, the residue is purified by distillation or recrystallization.

The reduction in process variant (c) is carried out in the customary manner, for example by reaction with a complex hydride, if appropriate in the presence of a diluent, or by reaction with aluminum isopropylate in the presence of a diluent.

If a complex hydride is used, possible diluents for the reaction according to the invention are polar organic solvents. These include, as preferences, alcohols, such as methanol, ethanol, butanol and isopropanol, and ethers, such as diethyl ether or tetrahydrofuran. The reaction is in general carried out at from 0° to 30° C., preferably at from 0° to 20° C. For this reaction, about 1 mol of a complex hydride, such as sodium hydride or lithium alanate, is preferably employed per mol of the ketone of the formula (Ia). To isolate the resultant compound of the formula (I), the residue is taken up in dilute hydrochloric acid and the mixture is then rendered alkaline and extracted with an organic solvent. Further working up is effected in the customary manner.

If aluminum isopropylate is used, preferred diluents for the reaction according to the invention are alcohols, such as isopropanol, or inert hydrocarbons, such as benzene. The reaction temperatures can again be varied within a substantial range; in general, the reaction is carried out between 20° and 120° C., preferably at from 50° to 100° C. For carrying out the reaction, about 1 to 2 mols of aluminum isopropylate are employed per mol of the ketone of the formula (Ia). To isolate the resultant compound of the formula (I), the excess solvent is removed by distillation in vacuo and the aluminum compound formed is decomposed with dilute sulphuric acid or sodium hydroxide solution. Further working up is effected in the customary manner.

The following acids can preferably be used for the preparation of physiologically acceptable acid addition salts of the compounds of the formula (I); hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal act on and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating cereal diseases, such as powdery mildew of cereal and powdery mildew of barley, Venturia species, such as the apple scab causative organism (*Fusicladium dendriticum*), and *Podosphaera* species, such as the powdery mildew of apple causative organism (*Podosphaera leucotricha*). It should be emphasised in particular that the active compounds according to the invention not only have a protective action but in some cases also have a systemic action. It is thus possible to protect plants from fungal attack if the active compound is fed to the above-ground parts of the plants via the soil and the root or via the seed.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

PREPARATIVE EXAMPLES

EXAMPLE 1

(a) Preparation of the precursor

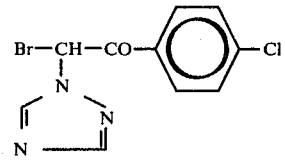

22.1 g (0.1 mol) of ω-(1,2,4-triazol-1-yl)-4-chloroacetophenone were dissolved in 150 ml of glacial acetic acid and, after adding 8.2 g (0.1 mol) of sodium acetate, 16 g (0.1 mol) of bromine were added dropwise at 45° C. until the mixture was completely decolorized. Thereafter, the reaction mixture was poured onto ice-water and extracted with chloroform. The organic phase was washed with sodium bicarbonate solution, dried over magnesium, sulphate and concentrated. Crude ω-bromo-ω-(1,2,4-triazol-1-yl)-4-chloroacetophenone, which was further reacted directly, was obtained in virtually quantitative yield.

(b)

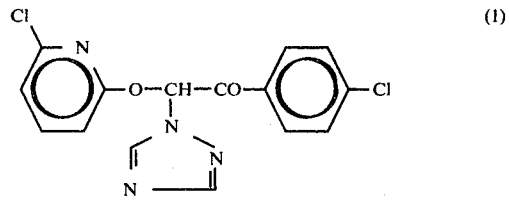

Process variant (a):

30 g (0.1 mol) of crude ω-bromo-ω-(1,2,4-triazol-1-yl)-4-chloroacetophenone were dissolved in 50 ml of acetonitrile and the solution was added to 13 g (0.1 mol) of 6-chloro-2-hydroxy-pyridine and 10.5 g (0.01 mol) of triethylamine in 120 ml of acetonitrile, while stirring. The mixture was heated under reflux for 1 hour and was then concentrated by distilling off the solvent in vacuo. The residue crystallized after stirring with water. Recrystallization from ethanol gave 23 g (66% of theory) of 1-(6-chloropyridin-2-yl-oxy)-2-(4-chlorophenyl)-1-(1,2,4-triazol-1-yl)-ethan-2-one of melting point 162° C.

EXAMPLE 2

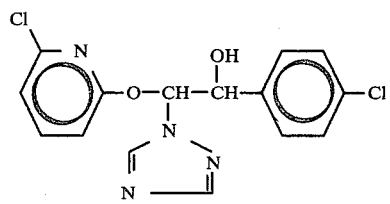 (2)

Process variant (c):

8.7 g (0.025 mol) of 1-(6-chloro-pyridin-2-yl-oxy)-2-(4-chlorophenyl)-1-(1,2,4-triazol-1-yl)-ethan-2-one (Example 1) were dissolved in 100 ml of methanol, and 1 g (0.025 mol) of sodium borohydride was added. The mixture was heated under reflux for 30 minutes and concentrated by distilling off the solvent in vacuo, and the residue was partitioned between chloroform and water. The organic phase was separated off, extracted again by shaking with water, dried over magnesium sulphate and concentrated. 62 g (70% of theory) of 1-(6-chloro-pyridin-2-yl-oxy)-2-(4-chlorophenyl)-1-(1,2,4-triazol-1-yl)-ethan-2-ol were obtained as a viscous oil.

The following compounds of the general formula

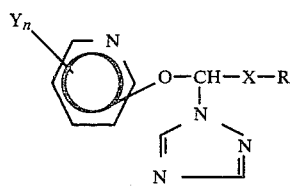 (I)

were obtained analogously, and according to process variants (a), (b) and (c):

| Compound No. | Y_n—pyridine | X | R | Melting point (°C.) |
|---|---|---|---|---|
| 3 | F (pyridyl) | CO | 2,3-Cl₂-phenyl | 103 |
| 4 | Cl (pyridyl) | CO | 2,4-Cl₂-phenyl | 136 |
| 5 | Cl (pyridyl) | CO | phenyl | 116 |
| 6 | F (pyridyl) | CO | 4-Cl-phenyl | 115 |
| 7 | 3,5,6-Cl₃ (pyridyl) | CO | 4-Cl-phenyl | 138 |
| 8 | Cl (pyridyl) | CO | 4-Cl-phenyl | 96 |
| 9 | 3-Cl, 5-CH₃, 6-CN (pyridyl) | CO | 4-Cl-phenyl | 160 |
| 10 | Cl (pyridyl) | CO | 4-F-phenyl | 122 |
| 11 | F (pyridyl) | CO | 4-F-phenyl | 75–77 |
| 12 | 3,5,6-Cl₃ (pyridyl) | CO | 4-F-phenyl | 102 |
| 13 | 3,6-Cl₂ (pyridyl) | CO | 2-Cl-phenyl | 102 |
| 14 | 3-Cl, 5-CH₃, 6-CN (pyridyl) | CO | 2-Cl-phenyl | 131 |
| 15 | 3,5,6-Cl₃ (pyridyl) | CO | 2-Cl-phenyl | 160 |

-continued

| Compound No. | Y_n-pyridine ring | X | R | Melting point (°C.) |
|---|---|---|---|---|
| 16 | 2-Cl, 6-Me pyridine | CO | biphenyl | 110 |
| 17 | 2-F, 6-Me pyridine | CO | biphenyl | 130 |
| 18 | 2-Cl, 3-Br, 5-Br, 6-Me pyridine | CO | 4-Cl-phenyl | 158 |
| 19 | 2-Br, 6-Me pyridine | CO | phenyl | 148 |
| 20 | 2-I, 6-Me pyridine | CO | biphenyl | 159 |
| 21 | 2-Cl, 6-Me pyridine | CH(OH) | 2,4-Cl₂-phenyl | Oil |
| 22 | 2-F, 6-Me pyridine | CH(OH) | 2,4-Cl₂-phenyl | Oil |
| 23 | 6-Me pyridine | CO | phenyl | resin |
| 24 | 2-Cl, 3-Cl, 4-CH₃, 5-CN, 6-Me pyridine | CO | phenyl | 162 |
| 25 | 2-F, 6-Me pyridine | CH(OH) | 4-Cl-phenyl | 130 (A-Form)* |
| 26 | 2-F, 6-Me pyridine | CH(OH) | 4-Cl-phenyl | 125 (B-Form)* |
| 27 | 2-Cl, 6-Me pyridine | CH(OH) | 4-F-phenyl | 118 |
| 28 | 2-F, 6-Me pyridine | CH(OH) | 4-F-phenyl | 112 |
| 29 | 2-Cl, 6-Me pyridine | CH(OH) | biphenyl | 178 |
| 30 | 2-F, 6-Me pyridine | CH(OH) | biphenyl | 152 |

*A- and B-Form = the two geometric isomers

USE EXAMPLES

The fungicidal activity of the compounds of this invention is illustrated by the following biological examples, wherein the compounds according to the present invention are each identified by the number (given in brackets) from the preparative examples hereinabove.

The known comparison compounds are identified as follows:

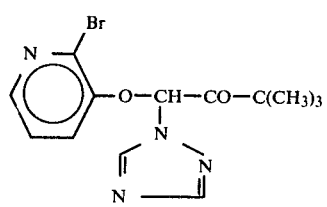

(A)

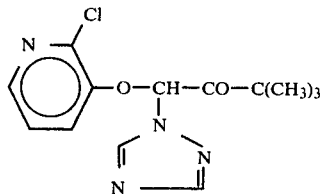

(B)

-continued (C) Structure: Cl-phenyl-O-CH(N-triazolyl)-CH(OH)-C(CH₃)₃

(D) Structure: I-phenyl-O-CH(N-triazolyl)-CO-C(CH₃)₃

EXAMPLE 3

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21–22 deg. C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compounds exhibited a very good action which was superior to that of the compounds (A) and (B) known from the prior art: compounds (3), (4), (1), (5) and (2).

EXAMPLE 4

Powdery mildew of barley (*Erysiphe graminis* var. *hordei*)

(fungal disease of cereal shoots)/systemic

The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3×12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. *hordei* and grown on at 21–22 deg. C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

In this test, for example, the following compounds exhibited a very good action which was superior to that of the compound (B) known from the prior art: compounds (3), (5) and (2).

EXAMPLE 5

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (*Fusicladium dendriticum*) and incubated for 18 hours in a humidity chamber at 18–20 degrees C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

In this test, for example, the following compounds exhibited a very good action which was superior to that of the compound (C) known from the prior art: compounds (3), (4) and (19).

EXAMPLE 6

Podosphaera test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 deg. C. and at a relative atmospheric humidity of 70%. They were then inoculated by dusting the conidia of the apple powdery mildew causative organism (*Podosphaera leucotricha*) and placed in a greenhouse at a temperature of 21–23 deg. C. and at a relative atmospheric humidity of about 70%.

10 days after the inoculation, the infection of the seedlings was determined. The assessment data were converted to % infection. 0% meant no infection; 100% meant that the plants were completely infected.

In this test, for example, the following compounds exhibited a very good action which was superior to that of the compounds (A) and (D) known from the prior art: compounds (3), (4), (5) and (2).

It will be appreciated that the instant specification and examples are set forth by way of illustration and not limitation, and that various modifications and changes may be made without departing from the spirit and scope of the present invention.

We claim:

1. A triazolyphenacyl pyridyl ether derivative of the formula

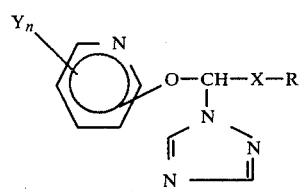

in which
R is phenyl, or phenyl substituted by one or more substituents selected independently from halogen, alkyl and alkoxy with in each case 1 to 4 carbon atoms, phenoxy, phenyl, halophenoxy and halophenyl,
X is —CO— or CH(OH)—,
Y each independently is halogen, alkyl or alkoxy with in each case 1 to 4 carbon atoms, or cyano, and
n is 0, 1, 2, 3 or 4,
or a physiologically acceptable addition product thereof with an acid or metal salt.

2. A compound according to claim 1, in which
the acid of the addition salt when present is selected from hydrogen halide acids, sulphuric acid, phosphoric acid, nitric acid, sulphonic acids and monofunctional or bifunctional carboxylic or hydroxycarboxylic acids, and
the metal salt when present comprises as metal copper, zinc, manganese, magnesium, tin, iron or nickel, and as the anion halide, nitrate, phosphate or sulphate.

3. A compound according to claim 1, wherein such compound is 1-(6-chloropyridin-2-yl-oxy)-2-(4-chlorophenyl)-1-(1,2,4-triazol-1-yl)-ethan-2-one of the formula

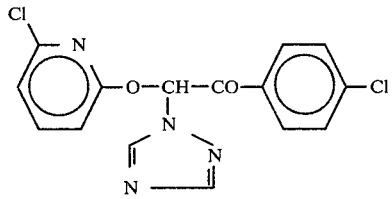

or a physiologically acceptable addition product thereof with an acid or metal salt.

4. A compound according to claim 1, wherein such compound is 1-(6-chloropyridin-2-yl-oxy)-2-(4-chlorophenyl)-1-(1,2,4-triazol-1-yl)-ethan-2-ol of the formula

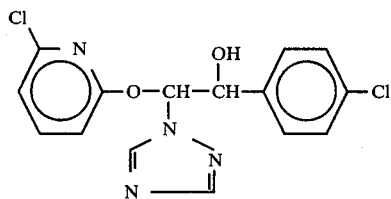

or a physiologically acceptable addition product thereof with an acid or metal salt.

5. A compound according to claim 1, wherein such compound is 1-(6-chloropyridin-2-yl-oxy)-2-(2,4-dichlorophenyl)-1-(1,2,4-triazol-1-yl)-ethan-2-one of the formula

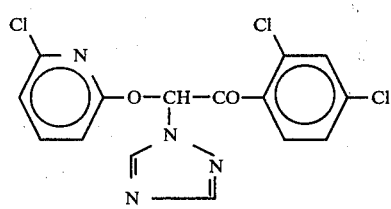

or a physiologically acceptable addition product thereof with an acid or metal salt.

6. A compound according to claim 1, wherein such compound is 1-(6-chloropyridin-2-yl-oxy)-2-phenyl-1-(1,2,4-triazol-1-yl-ethan-2-one of the formula

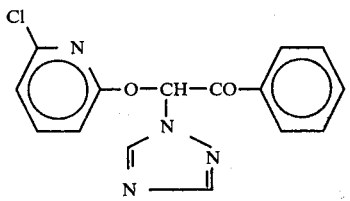

or a physiologically acceptable addition product thereof with an acid or metal salt.

7. A compound according to claim 1, wherein such compound is 1-(6-fluoropyridin-2-yl-oxy)-2-(4-chlorophenyl)-1-(1,2,4-triazol-1-yl)-ethan-2-one of the formula

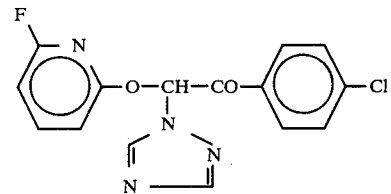

or a physiologically acceptable addition product thereof with an acid or metal salt.

8. A fungicidal composition comprising a fungicidally effective amount of a compound or addition product thereof according to claim 1 in admixture with a diluent.

9. A method of combating fungi, characterized in that there is applied to the fungi, or to a habitat thereof, a fungicidally effective amount of a compound or addition product thereof according to claim 1.

10. The method according to claim 9, wherein the material applied is
1-(6-chloropyridin-2-yl-oxy)-2-(4-chlorophenyl)-1-(1,2,4-triazol-1-yl)-ethan-2-one,
1-(6-chloropyridin-2-yl-oxy)-2-(4-chlorophenyl)-1-(1,2,4-triazol-1-yl)-ethan-2-ol,
1-(6-chloropyridin-2-yl-oxy)-2-(2,4-dichlorophenyl)-1-(1,2,4-triazol-1-yl)-ethan-2-one,
1-(6-chloropyridin-2-yl-oxy)-2-phenyl-1-(1,2,4-triazol-1-yl)-ethan-2-one or
1-(6-fluoropyridin-2-yl-oxy)-2-(4-chlorophenyl)-1-(1,2,4-triazol-1-yl)-ethan-2-one,
or a physiologically acceptable addition product thereof with an acid or metal salt.

* * * * *

UNITED STATES PATENT AND TRADEMARK OFFICE
CERTIFICATE OF CORRECTION

PATENT NO. : 4,330,547
DATED : May 18, 1982
INVENTOR(S) : Udo Kraatz, et al.

It is certified that error appears in the above—identified patent and that said Letters Patent is hereby corrected as shown below:

Col 6, line 40   Delete "-HBR" and insert -- -HBr --

Col. 17, lines 1-8   Delete " 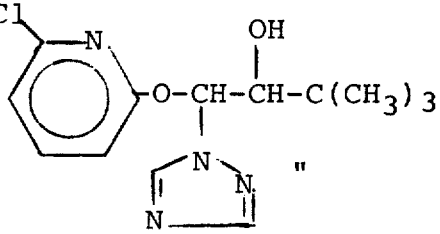 "

and insert --
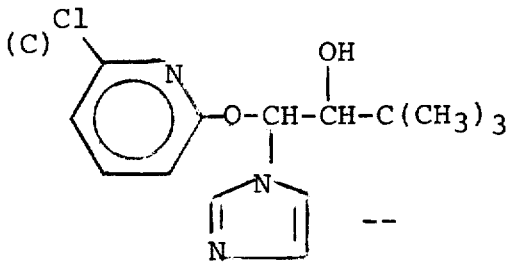
 --

Signed and Sealed this

Twentieth-eighth Day of September 1982

[SEAL]

Attest:

GERALD J. MOSSINGHOFF

Attesting Officer    Commissioner of Patents and Trademarks